(12) United States Patent
Dugstad et al.

(10) Patent No.: US 6,274,120 B1
(45) Date of Patent: Aug. 14, 2001

(54) DRY MICROPARTICLES FOR USE AS A CONTRAST AGENT

(75) Inventors: Harald Dugstad; Per Antonius Foss; Jo Klaveness, all of Oslo; Pål Rongved, Nesoddtangen; Roald Skurtveit, Oslo; Jan Solberg, Eiksmarka; Inger Reidun Fjeldskaar Aukrust, Lier, all of (NO)

(73) Assignee: Nycomed Imaging AS, Oslo (NO)

( * ) Notice: Subject to any disclaimer, the term of this patent is extended or adjusted under 35 U.S.C. 154(b) by 0 days.

(21) Appl. No.: 09/418,019

(22) Filed: Oct. 14, 1999

Related U.S. Application Data

(63) Continuation of application No. 08/468,741, filed on Jun. 6, 1995, now abandoned, which is a continuation of application No. PCT/GB95/00316, filed on Feb. 15, 1995.

(30) Foreign Application Priority Data

Feb. 15, 1994 (GB) .................................................. 9402867

(51) Int. Cl.$^7$ ............................ A61B 5/055; A61K 49/04; A61K 9/16

(52) U.S. Cl. ..................... 424/9.322; 424/9.32; 424/9.52; 424/9.5; 424/489

(58) Field of Search .................................. 424/9.52, 9.51, 424/9.5, 9.3, 9.32, 9.321, 9.322, 489, 498, 499, 491; 516/11, 77; 428/402

(56) References Cited

U.S. PATENT DOCUMENTS

| | | | |
|---|---|---|---|
| 5,215,680 | * | 6/1993 | D'Arrigo .............................. 252/307 |
| 5,639,443 | * | 6/1997 | Schutt et al. ........................ 424/9.52 |

FOREIGN PATENT DOCUMENTS

93/17718 * 9/1993 (WO) ............................. A61K/49/00

* cited by examiner

Primary Examiner—Michael G. Hartley
(74) Attorney, Agent, or Firm—Royal N. Ronning, Jr.

(57) ABSTRACT

Microparticulate contrast agents comprising gas or a gas precursor encapsulated by a non-polymeric and non-polymerisable wall-forming material are readily characterisable materials exhibiting surprising structural integrity and stability.

8 Claims, No Drawings

DRY MICROPARTICLES FOR USE AS A CONTRAST AGENT

This application is a Continuation of nonprovisional application Ser. No. 08/468,741 filed Jun. 6, 1995, now abandoned; which is a Continuation of International Patent Appl. PCT/GB95/00316 filed on Feb. 15, 1995.

This invention relates to novel contrast agents, more particularly to new gas-containing and gas-generating contrast agents of use in diagnostic imaging, and to methods for their preparation and use.

It is well known that ultrasonic imaging comprises a potentially valuable diagnostic tool, for example in studies of the vascular system, particularly in cardiography, and of tissue microvasculature. A variety of contrast agents has been proposed to enhance the acoustic images so obtained, including suspensions of solid particles, emulsified liquid droplets, gas bubbles and encapsulated gases or liquids. It is generally accepted that low density contrast agents which are easily compressible are particularly efficient in terms of the acoustic backscatter they generate, and considerable interest has therefore been shown in the preparation of gas-containing and gas-generating systems.

Gas-containing contrast media are also known to be effective in magnetic resonance (MR) imaging, e.g. as susceptibility contrast agents which will act to reduce MR signal intensity. oxygen-containing contrast media also represent potentially useful paramagnetic MR contrast agents.

Furthermore, in the field of X-ray imaging it has been observed that gases such as carbon dioxide may be used as negative oral contrast agents.

Initial studies involving free gas bubbles generated in vivo by intracardiac injection of physiologically acceptable substances have demonstrated the potential efficiency of such bubbles as contrast agents in echocardiography; such techniques are severely limited in practice, however, by the short lifetime of the free bubbles. Interest has accordingly been shown in methods of stabilising gas bubbles for echocardiography and other ultrasonic studies, for example using emulsifiers, oils, thickeners or sugars, or by entraining or encapsulating the gas or a precursor therefore in a variety of systems, e.g. as porous gas-containing microparticles or as encapsulated gas microbubbles.

Previous proposals relating to microbubble-containing ultrasound contrast agents have invariably required the use of a polymeric encapsulating coating for the microbubbles. Thus, for example, WO-A-8002365, which in principle suggests use of microbubbles having a coalescence resistant encapsulating membrane comprising non-toxic and non-antigenic organic molecules, in practice discloses only the use of gelatin as the encapsulating material. It has been found that microbubbles so encapsulated do not exhibit adequate stability at the dimensions preferred for use in echocardiography (1–10 μm) in view of the extreme thinness of the encapsulating coating.

U.S. Pat. No. 4,774,958 discloses the use of microbubble dispersions stabilised by encapsulation in denatured protein, e.g. human serum albumin. Such systems permit the production of microbubble systems having a size of e.g. 2–5 μm but still do not permit efficient visualisation of the left heart and myocardium. The use of such protein-derived agents may also create problems with regard to potential allergenic reactions.

EP-A-0327490 and WO-A-8906978 disclose, inter alia, ultrasonic contrast agents comprising microparticulate amylose or a synthetic biodegradable polymer containing a gas or volatile fluid (i.e. having a boiling point below 60° C.) in free or bonded form. Representative synthetic biodegradable polymers include polyesters of hydroxy carbonic acids, polyalkyl cyanoacrylates, polyamino acids, polyamides, polyacrylated saccharides and polyorthoesters.

Similar biodegradable microparticulate polymers, based on polymerised aldehydes, are described in EP-A-0441468, while systems based on microparticulate poly (amino acid)—poly (cyclic imide) derivatives are described in EP-A-0458079, U.S. Pat. No. 5,137,928, U.S. Pat. No. 5,190,982, U.S. Pat. No. 5,205,287 and U.S. Pat. No. 5,229,469.

EP-A-0458745 discloses air or gas-filled microballoons in which the encapsulating material is a deformable and resilient interfacially deposited polymer which is preferably biodegradable, examples including polysaccharides, polyamino acids, polylactides, polyglycolides, lactide/lactone copolymers, polypeptides, proteins, polyorthoesters, polydioxanone, poly-β-aminoketones, polyphosphazenes, polyanhydrides and poly (alkyl cyanoacrylates). The microballoons are normally prepared by emulsion techniques leading to deposition of the polymer around droplets of a volatile liquid which is subsequently evaporated. Such techniques generally involve the use of surfactants, for example lecithins, fatty acids or esters thereof with polyoxyalkylene compounds such as polyoxyethylene glycol or polyoxypropylene glycol, in order to stabilise the emulsion.

It is generally acknowledged that polymer-based contrast agents should desirably be biodegradable in order to facilitate their ultimate elimination from or absorption by the test subject. In many instances it has therefore been proposed to use polymers such as polyesters, polyanhydrides, polycarbonates, polyamides and polyurethanes which are biodegradable as a result of the susceptibility of ester, amide or urethane groups therein to enzymic hydrolysis in vivo.

In WO-A-9317718 there are described polymer-based contrast agents which are designed to exhibit high and controllable levels of biodegradability in vivo by virtue of the presence in the polymer of methylene diester units of formula (I)

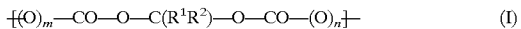

$$\text{-}(O)_m\text{-}CO\text{-}O\text{-}C(R^1R^2)\text{-}O\text{-}CO\text{-}(O)_n\text{-} \qquad (I)$$

(where $R^1$ and $R^2$ each represent a hydrogen atom or a carbon-attached monovalent organic group or $R^1$ and $R^2$ together form a carbon-attached divalent organic group and m and n, which may be the same or different, are each zero or 1). Such units are particularly rapidly degraded by common esterase enzymes but are relatively stable in the absence of enzymes.

In all the above-described encapsulated microbubble contrast agents the material encapsulating the microbubbles consists essentially of polymer, although minor quantities of other materials may be present. Thus, for example, EP-A-0458745 suggests that additives such as fats, waxes, high molecular weight hydrocarbons, phospholipids and plasticisers may be incorporated into the polymer wall, e.g. in amounts of up to 20% by weight. Clearly, however, it has hitherto been thought necessary to employ polymeric encapsulating material, e.g. in order to achieve sufficient structural integrity so as to impart adequate stability to the contrast agent. An isolated exception is WO-A-9401140, which discloses micro-gas bubble-containing echographic contrast agents prepared by lyophilising aqueous emulsions containing a lipid-soluble or water-insoluble builder such as cholesterol; these contrast agents are, however, also required to contain a substantial proportion of an apolar liquid such as petroleum ether.

We have now most surprisingly found that effective contrast agents comprising encapsulated microbubbles may be prepared using a wide range of non-polymeric wall-forming materials to encapsulate the gas or a precursor therefor. It will be appreciated that such contrast agents may exhibit significant advantages over polymer-based contrast agents, in particular that they may be easier and more economical to prepare and easier to characterise; they may also be more readily eliminable from the bodies of subjects to whom they are administered, for example by virtue of the smaller size and/or enhanced biodegradability of the non-polymeric molecules. The selection of materials which are endogeneous or are biodegradable to endogenous substances may also be advantageous.

Thus according to one aspect of the present invention there is provided a microparticulate contrast agent comprising gas or a gas precursor encapsulated by a non-polymeric and non-polymerisable wall-forming material.

The term "non-polymeric" as used herein denotes that the wall-forming materials do not contain multiple repeating units joined head-to-tail, as in polymers, and are not obtained by polymerisation techniques. The wall-forming materials will thus most commonly comprise well-defined and characterisable molecules, e.g. as evidenced by precise melting points, single chromatographic mobilities etc., and by monodisperse molecular weights (i.e. having a polydispersity index of 1.0, where this is defined as the ratio of weight average molecular weight to number average molecular weight), although it will be appreciated that the invention also embraces, for example, contrast agents comprising clearly constituted mixtures of such substances, including naturally occurring mixtures. These properties may be contrasted with those of materials obtained by polymerisation techniques, where products will typically comprise variable mixtures of molecules of different chain length and so will be characterised by a melting point range, a plurality of chromatographic mobilities and a molecular weight range (e.g. as evidenced by a polydispersity index higher than 1.0)

The term "non-polymerisable" indicates that the encapsulating material will not polymerise under, for example, conditions such as those used during preparation and storage of the contrast agents of the invention.

The encapsulating material may conveniently have a low molecular weight, for example in the range 100–6000. It will be appreciated that the molecular weight should be such that the melting point and solubility properties of the material permit microparticle formation at an appropriate temperature and under appropriate processing conditions, e.g. as described hereinafter.

It will be appreciated that in order to exhibit the necessary wall-forming properties the encapsulating material should be solid or semi-solid at normal storage and handling temperatures; the material therefore advantageously has a melting point of at least 40° C.; in many cases such materials will exhibit film-forming properties, which may be enhanced by virtue of the material having a somewhat amphiphilic character as a result of the presence of hydrophilic and lipophilic regions within the molecules; the hydrophilic character may for example derive from specifically hydrophilic groups such as carboxy, keto, hydroxy or amino and/or from the presence of groups enabling participation in hydrogen bonding, for example the carbonyl moieties of esterified carboxy groups.

In order to facilitate preparation of the contrast agents of the invention, e.g. by procedures such as those described hereinafter, the encapsulating material desirably has greater oil solubility than aqueous solubility.

In addition, the encapsulating material and any degradation products thereof which may be generated in vivo must be physiologically compatible and should either be endogenous or readily eliminable, optionally after breakdown into smaller molecules, e.g. as a result of hydrolytic, enzymatic or other metabolic reactions, for example involving labile linkages such as ester, amide or urethane groups.

The contrast agents of the invention may comprise a wide range of wall-forming materials which fulfil the above-described requirements, including, for example, fatty acids, e.g. lipophilic saturated or unsaturated aliphatic carboxylic acids containing 10–50 carbon atoms, e.g. 10–30 carbon atoms, such as palmitic, stearic or behenic acid, and esters thereof, e.g. alkyl esters, for example polyhydroxyalkyl esters such as pentaerythritol, ethylene glycol or glyceryl esters; fatty alcohols and amines, e.g. lipophilic saturated or unsaturated aliphatic alcohols and amines containing 10–50 carbon atoms. e.g. 10–30 carbon atoms, and esters or amides thereof, e.g. with mono-, di- or tri-carboxylic acids, for example optionally hydroxylated lower alkanoic acids such as acetic, adipic and citric acid; lipophilic aldehydes and ketones; lipophilic derivatives of sugars, e.g. containing liphophilic ether or, more preferably, ester groups; cholic acids and derivatives (e.g. esters) thereof; cholesterol and derivatives thereof; aliphatic and aromatic hydrocarbons such as mineral waxes; hydrophobically modified hydrophilic compounds, e.g. hydrophilic compounds such as X-ray contrast agents modified to contain one or more lipophilic groups (e.g. hydrocarbyl groups such as aliphatic chains) so as to render the molecule hydrophobic; and other biocompatible fat-soluble materials, e.g. antioxidants such as tocopherols or thioctic acid and derivatives thereof.

Contrast agents comprising wall-forming materials containing one or more methylene diester units (e.g. of formula (I) above) per molecule are useful embodiments of the invention by virtue of the ease with which they may be cleaved in vivo to form smaller and more readily eliminable molecules. Such units may also impart a desirable amphiphilic character to the wall-forming material.

Any biocompatible gas may be employed in the contrast agents of the invention, the term "gas" as used herein embracing any substance in gaseous form at 370° C. Representative gases include air, nitrogen, oxygen, hydrogen, nitrous oxide, carbon dioxide, helium, argon and low molecular weight hydrocarbons such as methane and acetylene. Low molecular weight fluorinated compounds such as sulphur hexafluoride, disulphur decafluoride, carbon tetrafluoride and perfluoroalkanes such as perfluoropropane, perfluorobutane and perfluoropentane may be of particular interest. The gas may be free within the microbubbles or may be trapped or entrained within a containing substance.

Contrast agents according to the invention may be used in a variety of diagnostic imaging techniques, including ultrasound, MR and X-ray imaging. Their use in diagnostic ultrasound imaging and in MR imaging, e.g. as susceptibility contrast agents, constitute preferred features of the invention.

For ultrasound applications such as echocardiography, in order to permit free passage through the pulmonary system and to achieve resonance with the preferred imaging frequency of about 0.1–15 MHz, it may be convenient to employ microparticles having an average size of 0.1–10 $\mu$m, e.g. 1–7$\mu$m. Substantially larger particles or bubbles, e.g. with average sizes of up to 500 $\mu$m, may however be useful in other applications, for example gastrointestinal imaging or investigations of the uterus or Fallopian tubes.

The contrast agents of the invention may be formulated in any manner appropriate to the intended method of administration, e.g. as suspensions in injectable media such as sterile water for injection. Such formulations may if desired contain biocompatible additives, e.g. antioxidants such as tocopherols or thioctic acid.

The contrast agents of the invention may be prepared by any convenient method, for example by techniques analogous to those described in WO-A-9317718. Representative techniques for the preparation of materials encapsulated by a wall or membrane are also described in literature such as "Microencapsulation and Related Drug Processes" by P. D. Deasy, Marcel Dekker Inc., New York (1984).

Thus, for example, contrast agents according to the invention may be prepared by emulsion techniques analogous to those in the polymer art. Typically such processes may involve (i) generating an emulsion comprising hydrophilic and hydrophobic phases wherein the wall-forming material is preferentially solubilised in the dispersed phase or is distributed about the interfaces between the phases, and (ii) isolating the desired contrast agent from the emulsion. The emulsion will preferably also comprise one or more emulsifiers solubilised in either or both phases. Single or multiple emulsions may be generated; representative emulsion techniques are described in WO-A-9317718.

The wall-forming material may be selected to have a lyophilicity appropriate to a particular form of emulsion processing; thus, for example, it may be advantageous to select an oil-soluble wall-forming material for processing using an oil-in-water emulsion. Oil-in-water emulsions may also be used to process wall-forming materials having a degree of water-solubility where the material exhibits attractive interactions sufficient to slow the kinetics of dissolution so as to permit microparticle formation in the presence of water; a similar approach may be taken using a water-in-oil emulsion and a wall-forming material having a degree of oil-solubility.

Emulsions may be prepared by, for example, conventional techniques such as agitation, sonication, stirring (preferably high speed stirring) or other forms of mixing (e.g. high shear mixing), membrane emulsification, high-voltage emulsification or high pressure homogenisation. The wall-forming material may advantageously be predissolved in what is to be the dispersed phase. As noted above, one or more emulsifiers may advantageously be solubilised in either or both phases of the emulsion; preferably at least one emulsifier is solubilised in the continuous phase.

It will be appreciated that factors such as stirring speed will influence the size of the encapsulated microbubbles ultimately produced; thus, for example, faster stirring will tend to yield smaller microbubbles. The amount of emulsifier employed may vary widely, but typically may equal or exceed the amount of wall-forming material on a weight basis. Additives such as emulsification assistants, e.g. viscosity enhancers such as proteins, carbohydrates, polysaccharides or other hydrophilic polymers, may if desired also be employed.

In an alternative procedure a solution of wall-forming material in an appropriate aprotic organic solvent (e.g. a sulphoxide such as dimethyl sulphoxide, a cyclic ether such as tetrahydrofuran or an N,N-disubstituted amide such as dimethylformamide) may be mixed with an aqueous phase (e.g. using a high speed stirrer) so as to precipitate wall-forming material, which may be collected and lyophilised to yield the desired contrast agent. The aqueous phase may advantageously contain a polymeric material such as polyvinyl alcohol or a poloxamer (e.g. a Pluronic). Such techniques are described in the above-mentioned EP-A-0458079.

A further process comprises injecting a solution of the wall-forming material in an appropriate aprotic solvent into liquid nitrogen; the solution may, if desired, also contain an additive such as hydroxypropylcellulose. Alternatively the wall-forming material may be dissolved in an appropriate solvent or dispersed in, for example, an oil-in-water, water-in-oil or multiple emulsion, and the solution or emulsion spray dried, e.g. as described in EP-A-0514970.

Coacervation techniques, e.g. as are known in the art, may also be employed in preparing contrast agents according to the invention.

In principle any emulsifier may be used in the preparation of contrast agents according to the invention. We have found that it may, however, be advantageous to select a polymeric emulsifier, since the stability of the contrast agents so obtained may thereby be enhanced, e.g. as evidenced by long-lasting retention of gas content coupled with a lower or minimal tendency of the microparticles to aggregate. Examples of such polymeric emulsifiers include polyvinyl alcohol, proteins (e.g. gelatin, albumins such as human or porcine serum albumin, and casein salts such as sodium caseinate), polysaccharides (e.g. modified chitosan, modified starches including lipophilised starch and soluble reduced amylose, heparin, and gums such as gum arabic), block copolymers consisting of alternating hydrophilic and hydrophobic blocks (e.g. polyhydroxystearate—polyethylene oxide block copolymers such as B246 (117753-68-1), polyoxyethylene—polyoxypropylene block copolymers, including poloxamers such as tetronics and Pluronic F38, F68, F77, F88, F127, L44, L64, P84 or P123, or perfluorinated derivatives thereof), polyoxyethylated derivatives of partial fatty acid esters of hexahydric alcohols such as sorbitol (e.g. Tween-type surfactants such as Tween 40, 60 or 80), polyvinylpyrrolidones (e.g. Kollidon), fatty alcohol ethers of polyoxyethylene alcohols (e.g. Brij-type surfactants such as Brij 52 or 99), polyethylene glycol esters of fatty acids (e.g. Cremaphor-type surfactants such as Cremaphor RH40), polyethylene glycol—sorbitan—beeswax surfactants such as Atlas G-1702 (PEG-6 sorbitan beeswax) and Atlas G-1726 (PEG-20 sorbitan beeswax), and perfluorinated derivatives of any of the above polyethylene glycol-containing compounds.

While we do not wish to be bound by theoretical considerations, it may be that such polymeric emulsifiers are particularly compatible with the wall-forming material and may, for example, be present as external coatings on the encapsulating material in contrast agents according to the invention. As such they may, for example, enhance the subsequent dispersibility and stability of the contrast agents, e.g. inhibiting aggregative tendencies through electrostatic or other interactions. It will be appreciated that in such contrast agents the role of the emulsifier is as an emulsification aid and/or stabiliser and that it does not act as a wall-forming material.

It will be appreciated that the water-immiscible solvent used in emulsification procedures to prepare contrast agents according to the invention should be liquid at the temperature used for the emulsification process; it may advantageously be selected to have a vapour pressure which facilitates its removal at a later stage. Representative solvents include aliphatic, cycloaliphatic and araliphatic hydrocarbons, e.g. containing up to 16 carbon atoms, such as n-octane, cyclooctane, a dimethylcyclohexane, ethylcyclohexane, a methylheptane, an ethylhexane, toluene, xylene, naphthalene or a terpene, terpenoid or isoprenoid such as camphene or limonene; haloalkanes such as Freons, methylene chloride, chloroform, carbon tetrachloride or methyl bromide; esters such as ethyl or propyl acetate, butyl formate and propyl or isopropyl butyrate or isobutyrate; and appropriate ethers and other substances which are liquid and have appropriate dissolving properties at the temperature used for the emulsification process.

Where in the preparation of contrast agents according to the invention it is desired to deposit wall forming material at the interface between the oil and water phases of an emulsion, such deposition may be induced by, for example, modifying parameters such as temperature, pH, solvent properties or solute concentrations. Thus, for example, it is possible to induce the wall-forming material to precipitate by reducing the temperature of the emulsion, by pH change, by adding a non-solvent for the wall-forming material, or by at least partial removal of at least the organic solvent (e.g. by evaporation or lyophilisation, preferably under an atmosphere of the gas which is desired to be incorporated, for example as described in BP-A-0458745).

Where it is desired to prepare a gas precursor-containing contrast agent the precursor may, for example, conveniently be dissolved in the water-immiscible organic solvent prior to emulsification. The gas precursor may, for example, be a compound which reacts to produce gas following administration to a subject, e.g as a result of decomposition induced thermally or by pH change or as a result of enzymatic degradation. Thus, for example, non-toxic organic carbonates and bicarbonates, e.g arginine carbonate and compounds of formula RO.CO.OM where R is an organic group and M represents a physiologically acceptable cation, will generate carbon dioxide in the conditions of pH prevailing in the bloodstream, as will compounds such as aminomalonates.

In general, the contrast agent may be isolated by any convenient method, for example by solvent removal using techniques such as evaporation, lyophilisation or spray drying. Such procedures may if desired be carried out under an atmosphere of the gas which is to be incorporated in the contrast agent, if desired at reduced pressure.

Contrast agents so obtained may be stored and transported in dry form, in which condition they may be stable indefinitely, being mixed with an appropriate liquid carrier (e.g. sterile water for injection, physiological saline or phosphate buffer) prior to administration. In this way the concentration of the injected or otherwise administered contrast agent may be varied at will depending on the precise nature of the application. The contrast agents may also be stored as suspensions in such carriers, especially where the porosity of the encapsulating membrane is comparatively low.

The following non-limitative Examples serve to illustrate the invention.

EXAMPLE 1

Synthesis of Wall-forming Materials and Emulsifiers a) Methylene bis(16-hexadecanoyloxyhexadecanoate)

A mixture of methylene bis(16-hydroxyhexadecanoate) (1.0 mmol) and palmitoyl chloride (7.0 mmol) was refluxed in diethyl ether (10 ml) for 24 hours before the solvent was evaporated. The residual material was purified on a silica gel flash column eluting first with hexane/chloroform (2:1) and then with chloroform. Yield 88%, white solid. $^1$H NMR (CDCl$_3$): δ 0.88 (6 H, t, J 6.7 Hz), 1.2–1.4 (92 H, m), 1.5–1.7 (12 H, m), 2.28 (4 H, t, J 7.5 Hz), 2.35 (4 H, t, J 7.6 Hz), 4.05 (4 H, t, J 6.7 Hz), 5.75 (2 H, s). $^{13}$C NMR (CDCl$_3$): δ 14.11, 22.70, 24.64, 25.06, 25.97, 28.70, 29.04, 29.19, 29.25, 29.29, 29.38, 29.47, 29.50, 29.56, 29.62, 29.67, 29.70, 29.71, 31.94, 34.00, 34.43, 64.39, 79.06, 172.59, 173.97.

b) Methylene (16-hexadecanoyloxyhexadecanoate)(16'-hydroxyhexadecanoate)

A mixture of methylene bis(16-hydroxyhexadecanoate) (1.0 mmol) and palmitoyl chloride (1.0 mmol) was refluxed in diethyl ether (10 ml) for 24 hours before the solvent was evaporated. The residual material was purified by repeated filtration through silica gel using methylene chloride/acetonitrile (95:5) for elution. Yield 38%, white solid. $^1$H NMR (CDCl$_3$): δ 0.88 (3 H, t, J 6.7 Hz), 1.2–1.4 (69 H, m), 1.5–1.7 (10 H, m), 2.29 (2 H, t, J 7.5 Hz), 2.35 (4 H, t, J 7.6 Hz), 3.64 (2 H, t, J 6.6 Hz), 4.05 (2 H, t, J 6.7 Hz), 5.75 (2 H, s). $^{13}$C NMR (CDCl$_3$): δ 14.12, 22.71, 24.64, 25.06, 25.77, 25.97, 28.70, 29.04, 29.19, 29.24, 29.25, 29.30, 29.38, 29.46, 29.50, 29.56, 29.60, 29.61, 29.63, 29.64, 29.66, 29.67, 29.70, 29.71, 31.95, 32.85, 34.01, 34.44, 63.09, 64.41, 79.06, 172.51, 174.01.

c) Product from reaction of methylene (16-hexadecanoyloxyhexadecanoate) (16'-hydroxyhexadecanoate) with adipoyl chloride A solution of methylene (16-hexadecanoyloxyhexadecanoate)(16'-hydroxyhexadecanoate) (1.0 mmol) and adipoyl chloride (0.5 mmol) was refluxed in xylene/trichloroethylene (4:1, 20 ml) at 60° C. under reduced pressure (150 mBar) for 16 hours before the solvent was evaporated. The crude product was purified by flash chromatography on silica gel using methylene chloride/acetonitrile (97:3) for elution. Yield 74%, white solid. $^1$H NMR (CDCl$_3$): δ 0.88 (6 H, t, J 6.7 Hz), 1.2–1.4 (136 H, m), 1.5–1.7 (24 H, m), 2.28 (4 H, t, J 7.5 Hz), 2.35 (12 H, t, J 7.6 Hz), 4.05 (8 H, t, J 6.7 Hz), 5.74 (4 H, 5). $^{13}$C NMR (CDCl$_3$) δ 14.12, 22.71, 24.48, 24.64, 25.06, 25.95, 25.97, 28.68, 28.70, 29.04, 29.19, 29.25, 29.30, 29.38, 29.47, 29.50, 29.56, 29.62, 29.67, 29.70, 29.72, 31.95, 33.98, 34.00, 34.43, 64.40, 64.56, 79.06, 172.49, 173.41, 173.98.

d) Methylene bis(16-hexadecanoyloxymethoxycarbonyloxyhexadecanoate)

i) Methylene bis(16-chloromethoxycarbonyloxyhexadecanoate)

Chloromethyl chloroformate (0.93 g, 7.2 mmol) was added to an ice-cooled solution of methylene bis(16-hydroxyhexadecanoate) (2.0 g, 3.6 mmol) in methylene chloride (80 ml). Pyridine (0.57 g, 7.2 mmol) was added and the reaction mixture was stirred for 15 minutes at 0° C. and 4 hours at room temperature The reaction mixture was washed with hydrochloric acid (1M, 50 ml) saturated aqueous sodium bicarbonate (50 ml), water (50 ml) and dried (MgSO$_4$). The solvent was evaporated and the residue was purified by flash chromatography (silica/methylene chloride). Yield: 84% $^1$H NMR (200 MHz, CDCl$_3$): δ 1.25 (m, 44H), 1.72 (m, 8H), 2.31 (t, 4H), 4.20 (t, 4H), 5.72 (m, 6H).

ii) Methylene bis(16-hexadecanoyloxymethoxycarbonyloxyhexadecanoate

Potassium t-butoxide (0.784 g, 7.0 mmol) was added to a solution of palmitic acid (1.80 g, 7.0 mmol) in N,N-dimethylformamide (100 ml), Methylene bis(16-chloromethoxycarbonyloxyhexadecanoate) (2.6 g, 3.5 mmol) in N,N-dimethylformamide (10 ml) was added to the resulting suspension, followed by 18-crown-6(0.1 g). The reaction mixture was stirred at room temperature for 2 days. The reaction mixture was filtered and the solvent was removed under reduced pressure. The residue was purified by flash chromatography (silica/methylene chloride). Yield: 19%. $^1$H NMR (300 MHz, CDCl$_3$):δ 0.86 (m, 6H), 1.23 (m, 12H), 1.62 (m, 92H), 2.33 (m, 8H), 4.16 (m, 4H), 5.73 (m, 6H).

e)1-(Octadecyloxycarbonyloxy)ethyl 5-acetamido-3-(N-methylacetamido)-2,4,6-triiodobenzenecarboxylate i) 1-Chloroethyl octadecyl carbonate 1-Chloroethyl chloroformate (7.15 g, 50 mmol) and 1-octadecanol (13.53 g, 50 mmol) were suspended in chloroform (100 ml) at 0° C. Pyridine (3.96 g, 50 mmol) was added dropwise during 20 minutes, maintaining the temperature below 10° C. After stirring at room temperature for 24 hours the reaction mixture was washed four times with 1N hydrochloric acid, once with a saturated sodium bicarbonate solution and finally twice with water. The organic solution was dried with magnesium sulphate and the solvent was removed at reduced pressure. Yield: 19 g.

ii) 1-(Octadecyloxycarbonyloxy)ethyl 5-acetamido-3-(N-methylacetamido)-2,4,6-triiodobenzenecarboxylate 1-Chloroethyl octadecyl carbonate (7.54 g, 20 mmol) was added at room temperature to a solution of potassium 5-acetamido-3-(N-methylacetamido)-2,4,6-triiodobenzenecarboxylate (15.99 g, 24 mmol) and potassium iodide (0.33 g, 2 mmol) in dry N,N-dimethylformamide. After stirring at 50° C. for 18 hours the solvent was removed at reduced pressure. The residue was suspended in chloroform (200 ml) and washed three times with a saturated sodium bicarbonate solution and finally twice with water. After drying with magnesium sulphate the solvent was removed at reduced pressure. Yield: 18.6 g. The product was further purified by flash chromatography (Silicagel 60, chloroform/acetonitrile 85:15). $^1$H NMR (DMSO-d$_6$): δ 0.852(CH$_2$CH$_3$), 1.236(CH$_2$), 1.639(CH CH$_3$),1.657(COOCH$_2$CH$_2$), 1.670(N(CH$_3$)COCH$_3$), 2.051 (NCOCH$_3$),2.965(NCH$_3$), 4.154(COOCH$_2$), 6.971 ( CHCH$_3$),10.103 (NH).

f) Methylene bis[3-(2.3-dihexadecanoyloxypropoxycarbonyl)propionate]

i) 3-(2.3-Dihexadecanoyloxypropoxycarbonyl) propionic acid

Dipalmitin (1,2-dipalmitoylglycerol),(3.00 g,5.27 mmol), succinic anhydride (1.00 g,10.0 mmol) and N,N-dimethyl-4-aminopyridine (50 mg, 0.41 mmol) were dissolved in tetrahydrofuran (30 ml) and N,N-dimethylformamide (10 ml) under a nitrogen atmosphere. Triethylamine (2.5 ml) was subsequently added and the resulting solution was stirred for two days at ambient temperature. The solvents were evaporated at reduced pressure and the white solid residue was redissolved in chloroform (150 ml). The solution was washed with it aqueous hydrochloric acid (10 ml) and with brine (2×50 ml), dried with magnesium sulphate and finally concentrated, yielding 5.80 g of a white solid which was used without further purification in the subsequent reaction.

$^1$H NMR (300 MRz, CDCl$_3$): δ 0.85–0.90 (m,6H), 1.20–1.35 (m, 48H), 1.55–1.65 (m,4H), 2.30 (dd, J$_1$=7.6,J$_2$=2.5 Hz, 2H), 2.32 (dd, J$_1$=7.4,J$_2$=2.3 Hz,2H), 2.62–2.70 (m,4H),4.14 (dd, J$_1$=12.1, J$_2$=5.9 Hz, 1H), 4.18 (dd, J$_1$=12.1, J$_2$=5.9 Hz, 1H), 4.29(dd, J$_1$=9.0, J$_2$=4.4 Hz, 1H), 4.33 (dd, J$_1$=9.0, J$_2$=4.4 Hz, 1H), 5.23–5.30 (m,1H). $^{13}$C NMR (300 MHz, CDCl$_3$): δ 14.121, 22.720, 24.890, 24.917, 28.716, 28.756, 29.110, 29.156, 29.310, 29.397, 29.517, 29.530, 29.697, 29.731, 31.961, 34.077, 34.211, 62.058, 62.673, 68.802, 171.620, 172.956, 173.349, 177.162.

ii) Methylene bis [3-(2.3-dihexadecanoyloxypropoxycarbonyl)propionate]

1,8-Diazabicyclo[5.4.0]undec-7-ene(633 mg, 4.158 mmol) was added to a solution of 3-(2,3-dihexadecanoyloxypropoxycarbonyl)propionic acid from (a) above (2.65 g, 3.96 mmol) in dry methylene chloride and N,N-dimethylformamide (40 ml, 1:1) under a nitrogen atmosphere. After 15 minutes stirring of the solution, diiodomethane (530 mg, 1.980 mmol) was added. The resulting solution was stirred at ambient temperature for four days, the solvents were evaporated at reduced pressure and the solid residue was redissolved in methylene chloride (200 ml). The solution was washed with 1% aqueous hydrochloric acid (1×25 ml) and brine (3×50 ml), dried with magnesium sulphate and concentrated, yielding 2.80 g of a yellowish waxy solid, containing two products and some remaining starting material as shown by thin layer chromatographic analysis. The crude mixture was purified by medium pressure chromatography using a silica column and gradient elution, with stepwise increasing concentration of ethyl acetate in petroleum ether, resulting in 1.07 g of the title compound as a white solid. $^1$H NMR (300 MHz, CDCl$_3$): δ 0.88 (t, J=7.2 Hz, 12H), 1.26 (m, 96H), 1.61 (m, 8H), 2.30 (dd, J$_1$=7.7, J$_2$=3.2 Hz, 4H), 2.32 (dd, J$_1$=7.4, J$_2$=3.7 Hz, 4H), 2.65–2.69 (m, 8 H), 4.14 (dd, J$_1$=11.8, J$_2$=3.0 Hz, 2H), 4.17(dd, J$_1$=11.2, J$_2$=2.95 Hz, 2H), 4.27–4.34 (m, 4H), 5.23–5.29 (m,2H), 5.77(s, 2H). $^{13}$C NMR (300 MHz, CDCl$_3$): δ 14.114, 22.714, 24.890, 24.910, 28.556, 28.756, 29.116, 29.156, 29.303, 29.317, 29.390, 29.517, 29.530, 29.657, 29.671, 29.691, 29.731, 31.954, 34.057, 34.197, 62.018, 62.719, 68.775, 79.444, 170.858, 171.440, 172.849, 173.209.

g) Methylene bis[16-(15-(16-hydroxyhexadecanoyloxymethoxycarbonyl) pentadecyloxycarbonylethylenecarbonyloxy)hexadecanoate i) Methylene bis[16-(carboxyethylenecarbonyloxy) hexadecanoate]

Methylene bis(16-hydroxyhexadecanoate) (5.5 g, 10 mmol), succinic anhydride (2.2 g, 22 mmol), and N,N-dimethyl-4-aminopyridine (2.5 g, 20 mmol) were dissolved in N,N-dimethylformamide (100 ml) and heated to 50° C. under stirring for 16 hours. N,N-dimethylformamide was evaporated in vacuo, the residue dissolved in chloroform/methanol (99:1) and filtered through a short silica column with the dissolving agent. The product was washed with petroleum ether, filtered, and dried under vacuum. Yield: 6 g white solid (78%) $^1$H NMR (CDCl$_3$): δ1.23–1.30 (m, 42H), 1.60–1.64 (m, 8H), 2.32–2.37 (t,4H), 2.62–2.69 (m, 10H), 4.06–4.09 (t,4H), 5.75 (s, 2H), 10–11 (m, 2H).

ii) Methylene bis [16-(15-(16-hydroxyhexadecanoyloxymethoxycarbonyl) pentadecyloxycarbonylethylenecarbonyloxy) hexadecanoate]

Methylene bis[16-(carboxyethylenecarbonyloxy) hexadecanoate] from (a) above (380 mg, 0.5 mmol), methylene bis(16-hydroxyhexadecanoate) (600 mg, 1.1 mmol), N-ethyl-N'-3-(3-dimethylaminopropyl)carbodiimide hydrochloride (200 mg,1.05 mmol), and N,N-dimethyl-4-aminopyridine (50 mg) were dissolved in 25 ml N,N-dimethylformamide and stirred at 45° C. for 16 hours. N,N-dimethylformamide was evaporated in vacuo, the residue dissolved in chloroform and purified by column chromatography on Silica KG60 with dichloromethane/methanol as eluant. Yield: 100 mg white solid; (10%). $^1$H NMR (CDCl$_3$): δ 1.25 (m,132H),1.59–1.65 (m, 24H), 2.32–2.37 (t, 12H), 2.61 (s, 8H), 3.63 (t,4H), 4.05–4.09 (t, 8H), 5.74 (s,6H).

h) 2-Hexadeylmalonic acid dihexadecyl ester 1,8-Diazabicyclo[5.4.0]undec-7-ene(1,5-5)(4.567 g, 30 mmol) and 1-iodohexadecane (10.570 g, 30 mmol) were added to a solution of 2-hexadecylmalonic acid in N,N-dimethylformamide (75 ml). After stirring at room temperature for 22 hours the precipitate was filtered off and washed with N,N-dimethylformamide. The product was purified by flash chromatography on silica gel using chloroform/hexane as eluant. Yield: 52%. $^1$H-NMR (300 MHz, CDCl$_3$): δ 0.88(t,9H), 1.26(m,80H), 1.62(m,4H), 1.88(m,2H), 3.31(t, 1H), 4.15(m,4H). FAB-MS: 799.7 (M+Na).

i) 2.2-Dihexadecylmalonic acid dihexadecyl ester

Sodium hydride (72 mg, 3 mmol) was added in portions to a cooled (ice/water) solution of 2-hexadecylmalonic acid dihexadecyl ester (2.33 g, 3 mmol) in tetrahydrofuran (45 ml) under an argon atmosphere and the resulting mixture was stirred at ambient temperature for 30 minutes. The solvent was evaporated and the solid residue was redissolved in N,N-dimethylformamide (45 ml). A solution of 1-iodohexadecane (1.06 g, 3 mmol) in N,N-dimethylformamide (20 ml) was added and stirring was continued at room temperature for 24 hours. Water (75 ml) was added to the reaction mixture after the pH had been adjusted to about 5 with 2N HCl. The mixture was extracted with chloroform (3×75 ml) and the chloroform phase was washed with water (3×75 ml). The organic phase was dried with magnesium sulphate and the solvent was removed at reduced pressure. The residue was purified by flash chromatography (silicagel 60, chloroform/hexane). Yield: 66%.
$^1$H-NMR (300 MHz, CDCl$_3$): δ 0.88(t,12H), 1.26(m,108H), 1.60(m,4H), 1.85(m,4H), 4.09(t,4H). FAB-MS: 1024 (M+Na).

j) 3-Hexadecyloxycarbonyl-3-hydroxypentanedioic acid dihexadecyl ester 1,8-Diazabicyclo[5.4.0]undec-7-ene(1,5-5)(4.567 g, 30 mmol) was added at room temperature to a solution of citric acid (1.924 g, 10 mmol) in N,N-dimethylformamide (50 ml). 1-Iodohexadecane (10.570 g, 30 mmol) was added and the resulting mixture was stirred at 50° C. for 21 hours. The precipitated product was filtered off and washed with N,N-dimethylformamide and the crude product was purified by flash chromatography on silica gel using chlorform/hexane for elution. Yield: 83%. $^1$H-NMR (300 MHz, CDCl$_3$): δ 088(t,9H), 1.26(m,78H), 1.60(m,6H), 2.84(q,4H), 4.07(t, 4H), 4.13(s,1H), 4.20(t,2H). FAB-MS: 887.6(M+Na).

k) Methylene bis-16-13-(2.3-bis-hexadecanoyloxypropoxy carbonyl)proanoyloxyl hexadecanoate Succinic acid 2,3-bis-hexadecanoyloxypropyl monester (1.30 g, 1.94 mmol) and methylene bis-16-hydroxyhexadecanoate (515 mg, 0.925 mmol) and triphenylphosphine (510 mg, 1.94 mmol) were dissolved in tetrahydrofuran (25 ml) under a nitrogen atmosphere. To the resulting solution was added diethyldiazodicarboxylate (as a 38–40% solution in toluene; 930 μl, 1.94 mmol). The resulting reaction mixture was stirred at ambient temperature for 24 hours then concentrated to dryness. The remaining solid was redissolved in toluene/methylene chloride (5:2) and charged on top of a short column of silica gel, gradient elution with increasing amount of ethyl acetate (from 0 to 40%) in petroleum ether and evaporation of the solvents affording 1.43 g of the title compound (83%) as a white solid (Mp 47° C.).
$^1$H NMR (300 MHz, CDCl$_2$): δ 0.88 (t,12H), 1.26 (m,140H), 1.62 (m, 16H), 2.28–2.38(m,12H), 2.61–2.65 (m, 8H), 4.08 (t, J=7 Hz, 4H), 4.14(dd, J$_1$=12 Hz, J$_2$=6 Hz, 2H), 4.18 (dd,J$_1$=12 Hz, J$_2$=6 Hz, 2H), 4.29(dd, J$_1$=12 Hz, J$_2$=4.5 Hz, 2H) 4.32 (dd, J$_1$=12, J$_2$=4.5 Hz, 2H) 5.23–5.32(m,2H), 5.74(s, 2H). $^{13}$C NMR(300 MHz, CDCl$_3$): δ 14.12, 22.71, 24.64, 24.87, 24.90, 25.91, 28.62, 28.94, 29.00, 29.04, 29.10, 29.14, 29.25, 29.30, 29.38, 29.48, 29.50, 29.52, 29.56, 29.62, 29.64, 29.68, 29.72, 31.95, 34.00, 34.06, 34.20, 62.04, 62.58, 65.00, 68.79, 76.63, 77.05, 77.47, 79.05, 171.83, 172.11, 172.48, 172.87, 173.24.
PD-MS: 1881 (M–H+23(Na)), 1603 (M–H+23(Na)–255), 906 (odd el. fragm. with H), 651 (even el fragm.). MALDI-MS: 1897 (M+39(K)), 1881 (M+23(Na)).

l) Ethylidene bis(16-acetoxyhexadecanoate)

i) Ethlidene bis 16-hydroxyhexadecanoate)

1,8-Diazabicyclo [5.4.0.]undec-7-ene (1,5-5) (2.74 g, 0.018 mol) was added to 16-hydroxyhexadecanoic acid (4.90 g, 0.013 mol) in dimethylformamide (150 ml). After 5 minutes with stirring ethylidene iodide (2.54 g, 0.009 mol) was added and the mixture was left with stirring at 40° C. for 3 days. The reaction mixture was cooled to 20° C. and when precipitation was complete (2 hours) the precipitate was isolated by filtration. The product was treated with activated carbon and recrystallised twice from dichworomethane to give 1.03 g (20%) of the title compound. Differential scanning calorimetry indicated that onset melting temperature was 88.93° C. $^1$H NMR (200 MHz, CDCl$_3$): δ 1.25 (s, 44H, CH$_2$), 1.45 (d, 3H, C$\underline{H}$$_3$CH) 1.56 (m, 8H, CH$_2$), 2.30 (t, 4H, CH$_2$CO), 3.63 (t, 4H, 2×CH$_2$O), 6.86 (q, 1H, C$\underline{H}$CH$_3$). $^{13}$C NMR (50 MHz, CDCl$_3$): δ 20.86, 25.91, 26.98, 30.22, 30.44, 30.67, 30.84, 34.00, 35.30, 64.00, 89.00, 171.77 (C=O).

ii) Ethylidene bis-(16-acetoxyhexadecanoate)

Ethylidene bis-16-hydroxyhexadecanoate (911 mg, 1.74 mmol) and N,N-dimethyl-4-aminopyridine (32 mg) were dissolved in tetrahydrofuran (25 ml), whereafter triethylamine (0.6 ml) and acetic anhydride (1 ml) were added successively via a syringe under a nitrogen atmosphere. After stirring the reaction mixture for two hours tit was diluted with methylene chloride and washed successively with hydrochloric acid (1%), saturated aqueous sodium bicarbonate and water. The organic phase was dried, the solvent was evaporated and the solid residue was dried under vacuum for a period of 24 hours yielding 1.07 g (94%) of the title compound as a white solid (MP 58° C.).
$^{13}$H NMR (300 MHz, CDCl$_3$): δ 1.26 (m,44H), 1.46 (d, J=5.5 Hz, 3H), 1.56–1.67(m, 8H), 2.04 (s, 6H), 2.27–2.33 (m, 4H), 4.05 (t, J=6.7 Hz, 4H), 6.86 (q, J=5.5 Hz, 1H). $^{13}$CNMR (300 MHz, CDCl$_3$): δ 19.58, 21.01, 24.68, 25.93, 28.64, 29.02, 29.26, 29.28, 29.47, 29.54, 29.59, 29.61, 29.65, 34.13, 64.66, 76.62, 77.04, 77.47, 88.31, 171.19, 171.73.

m) Ethylidene bis-(16-hexadecanoyloxyhexadecanoate)

Ethylidene bis-16-hydroxyhexadecanoate (570 mg, 1 mmol) was dissolved in 25 ml dichloromethane. Triethylamine (276 μl, 2 mmol) was added with stirring. Palmitoyl chloride (600 μl, 2 mmol) dissolved in dichloromethane (25 ml) was added dropwise with stirring. The reaction mixture was stirred overnight, whereafter the solvent was evaporated in vacuo; the residue was dissolved in dichloromethane and chromatographed on a glass column packed with silica. The produced was eluted with hexane/dichloromethane (1:2). Yield: 900 mg (85 t).
$^1$H-NMR (300 MHz, CDCl$_3$): δ=0.91–0.85(6H, m), 1.37–1.23 (91H, m), 1.47–1.45(3H, d), 1.67–1.55 (12H, m), 2.33–2.26(8H, m), 4.08–4.03(4H, t), 6.89–6.84(1H, t).

n) Methylene bis-(16-acetoxyhexadecanoate)

Methylene bis-16 hydroxyhexadecanoate (2.0 g, 3.47 mmol) and N,N-dimethyl-4-aminopyridine (50 mg) were dissolved in tetahydrofuran (25 ml), whereafter triethylamine (1.2 ml) and acetic anhydride (2 ml) were added successively via a syringe under a nitrogen atmosphere. After stirring the reaction mixture for two hours it was diluted with methylene chloride and washed successively with hydrochloric acid (1%), saturated aqueous sodium bicarbonate and water. The organic phase was dried, the solvent was evaporated and the solid residue was dried under vacuum for a period of 24 hours yielding 2.06 g (90%) of the title compound as a white solid.
$^1$H NMR (300 MHz, CDCl$_3$) δ 1.26 (m, 44H), 1.56–1.68 (m, 8H), 2.04 (s, 6H), 2.35(t, J=7.5 Hz, 4H), 4.05 (t, J=6.7 Hz, 4H), 5.74 (s, 2H). $^{13}$C NMR (300 MHz, CDCl$_3$): δ 21.00, 24.64, 25.94, 28.64, 29.03, 29.24, 29.28, 29.46, 29.54, 29.59, 29.60, 29.65, 29.66, 34.00, 64.66, 76.62, 77.04, 77.47, 79.06, 171.18, 172.49.

o) Methylene bis-16-[3-(2,3-bis-hexadecanoyloxy propoxycarbonyl)propanoyloxy]dodecanoate Succinic acid 2,3-bis-hexadecanoyloxypropyl monoester (324 mg, 0.485 mmol) and methylene bis-12-hydroxydodecanoate (135 mg, 0.304 mmol) and triphenylphosphine (127 mg, 0.485 mmol) were dissolved in tetrahydrofuran (5 ml) under a nitrogen atmosphere. To the resulting solution was added diethyldiazodicarboxylate as a 38–40% solution in toluene (233 µl, 0.485 mmol). The resulting reaction mixture was stirred at ambient temperature for 24 hours then concentrated to dryness. The remaining solid was redissolved in methylene/petroleum ether (4:1) and charged on top of a short column of silica gel, gradient elution with increasing amount of ethyl acetate (from 0 to 40%) in petroleum ether and evaporation of the solvents affording 283 mg (67%) of the title compound as a white solid.

$^1$H NMR (300 MHz, CDCl$_3$): δ 0.88 (t, 12H), 1.26 (m, 124H), 1.55–1.67 (m, 16H), 2.27–2.38 (m, 12H), 2.61–2.65 (m, 8H), 4.08 (t, J=7 Hz, 4H), 4.14 (dd, J$_1$=12 Hz, J$_2$=6 Hz, 2H), 4.18 (dd, J$_1$=12 Hz, J$_2$=6 Hz, 2H), 4.29 (dd, J$_1$=12 Hz, J$_2$=4.5 Hz, 2H), 4.32 (dd J$_1$=12 Hz, J$_2$=4.5 Hz, 2H), 5.23–5.32 (m, 2H), 5.74 (s, 2H) $^{13}$C NMR (300 MHz, CDCl$_3$): δ 14.13, 22.71, 24.62, 24.88, 24.90, 25.90, 28.60, 28.93, 29.00, 29.03, 29.10, 29.14, 29.23, 29.26, 29.30, 29.38, 29.42, 29.51, 29.68, 29.72, 31.95, 33.98, 34.06, 34.20, 62.04, 62.57, 64.98, 68.78, 76.63, 77.06, 77.48, 79.06, 171.84, 172.11, 172.46, 172.87, 173.24.

p) PEG 10000 methyl ether 16-hexadecanoylhexadecanoate

PEG 10000 methyl ether (7.500 g, 0.75 mmol) was dissolved in toluene (140 ml) and pyridine (0.107 g, 1.35 mmol) was added. The solution was heated to 60° C. and 16-hexadecanoyloxyhexadecanoyl chloride (0.595 g, 1.12 mmol) dissolved in toluene (10 ml) was added dropwise. The mixture was heated to reflux and after stirring under reflux for 3 days the mixture was cooled to room temperature and precipitated into hexane. After filtering, the precipitate was washed with hexane and is dried. Flash chromatography on a silica column, eluting with 5% methanol in chloroform, gave 5.39 g (68%) of the title compound. $^1$H NMR (300 MHz, CDCl$_3$): δ (0.84 (t, CH$_3$), 1.21 (s (br), CH$_2$), 1.55–1.60 (m, CH$_2$), 2.20–2.35 (m, CH$_2$CO), 3.34 (s, CH$_3$O), 3.61 (s, OCH$_2$CH$_2$O), 4.01 (t, COOCH$_2$CH$_2$O), 4.18 (t, COOCH$_2$CH$_2$O). $^{13}$C NMR (75 MHz, CDCl$_2$): δ 13.94, 22.48, 24.70, 24.82, 25.73, 28.94, 29.05, 29.14, 29.26, 29.33, 29.39, 29.45, 31.71, 34.00, 58.84, 63.14, 68.99, 69.36, 69.86, 69.97, 70.01, 70.36, 70.74, 70.82, 70.86, 71.72, 77.10, 173.62, 173.80.

EXAMPLE 2

Preparation of Gas-filled Microparticles

General procedure

A solution of the wall-forming substance in toluene was prepared. This solution was added to three times its volume of water containing a surfactant and mixed with a high speed rotor-stator mixer (8000–25000 rpm for 60–240 seconds). The resulting emulsion was frozen using a methanol/dry ice bath and lyophilised, resulting in a white powder.

| Example | Wall material | % wall material in toluene | Surfactant | surfactant (% in water) |
|---|---|---|---|---|
| 2a | Stearic acid | 10 | Gum arabic | 3 |
| 2b | Product Ex 1a | 5 | HSA | 5 |
| 2c | Product Ex 1b | 5 | HSA | 5 |
| 2d | Product Ex 1c | 5 | HSA | 5 |
| 2e | Product Ex 1e | 5 | HSA | 5 |
| 2f | Product Ex 1f | 5 | HSA | 5 |
| 2g | Product Ex 1h | 5 | HSA | 5 |
| 2h | Product Ex 1i | 5 | HSA | 5 |
| 2i | Product Ex 1j | 5 | HSA | 5 |
| 2j | Product Ex 1j | 5 | Ex. 1p | 1 |
| 2k | Product Ex 1j | 5[1] | HSA | 5 |
| 2l | Product Ex 1j | 5[2] | HSA | 5 |
| 2m | Product Ex 1k | 5 | HSA | 5 |
| 2n | Product Ex 1l | 5 | HSA | 5 |
| 2o | Product Ex 1m | 5 | HSA | 5 |
| 2p | Product Ex 1n | 5 | HSA | 5 |
| 2q | 1-Octadecanol | 5 | HSA | 5 |
| 2r | Trimethylolethane | 5 | HSA | 5 |
| 2s | Cholesteryl palmitate | 5 | HSA | 5 |
| 2t | α-Palmitin | 5 | HSA | 5 |
| 2u | α,β-Dipalmitin | 5 | HSA | 5 |
| 2v | Tripalmitin | 5 | HSA | 5 |
| 2w | 2-Hexadecanone | 5 | HSA | 5 |
| 2x | Stearyl stearate | 5 | HSA | 5 |
| 2y | Nonadecanoic acid N-methylamide | 5 | HSA | 5 |

[1] Xylene as solvent
[2] Camphene as solvent
HSA = human serum albumin

EXAPLE 3

Acoustic Characterisation (In vitro)

The lyophilised samples from Example 2 were re-dispersed in MilliQ water or 0.9% sodium chloride solution by shaking on a laboratory shaker for an appropriate time. The particles were visually inspected using a light microscope.

The acoustic effect of the suspensions was obtained by measuring ultrasonic transmission through suspensions of different concentrations in an aqueous matrix, using either a 3.5 MHz broadband transducer in a pulse-reflection technique or two transducers with centre frequencies 3.5 and 5 MHz, covering a range from 1.5 to 8 MHz. The aqueous solvent system was used as reference, and measurements were performed by stepwise dilution of the starting suspension with the carrier liquid. Measurements were done until the signal was an acoustic attenuation of less than 0.1 db/cm.

| Example | Particles from Ex. 2 dispersed in (solvent) | Particle size (µm) | Result |
|---|---|---|---|
| 3a | 2a (H$_2$O) | 2–10 | Contrast |
| 3b | 2b (H$_2$O) | 2–10 | Strong Contrast |
| 3c | 2c (0.9% NaCl) | 3–5 | Strong Contrast |
| 3d | 2d (0.9% NaCl) | 3–5 | Strong Contrast |
| 3e | 2e (H$_2$O) | 2–10 | Strong Contrast |
| 3f | 2f (0.9% NaCl) | 1–5 | Strong Contrast |
| 3g | 2g (0.9% NaCl) | 2–10 | Strong Contrast |

-continued

| Example | Particles from Ex. 2 dispersed in (solvent) | Particle size (μm) | Result |
|---|---|---|---|
| 3h | 2h (0.9% NaCl) | 2–10 | Strong Contrast |
| 3i | 2i (0.9% NaCl) | 2–10 | Strong Contrast |
| 3j | 2j (0.9% NaCl) | 1–5 | Contrast |
| 3k | 2k (0.9% NaCl) | 1–5 | Strong Contrast |
| 3l | 2l (0.9% NaCl) | 2–5 | Contrast |
| 3m | 2m (0.9% NaCl) | 2–10 | Strong Contrast |
| 3n | 2n (0.9% NaCl) | 1–10 | Contrast |
| 3o | 2o (0.9% NaCl) | 2–10 | Strong Contrast |
| 3p | 2p (0.9% NaCl) | 1–5 | Contrast |
| 3q | 2q (0.9% NaCl) | 1–10 | Contrast |
| 3r | 2r (0.9% NaCl) | 1–5 | Contrast |
| 3s | 2s (0.9% NaCl) | 2–10 | Strong Contrast |
| 3t | 2t (0.9% NaCl) | 2–15 | Contrast |
| 3u | 2u (0.9% NaCl) | 2–10 | Strong Contrast |
| 3v | 2v (0.9% NaCl) | 2–10 | Strong Contrast |
| 3w | 2w (0.9% NaCl) | 2–10 | Contrast |
| 3x | 2x (0.9% NaCl) | 2–10 | Strong Contrast |
| 3y | 2y (0.9% NaCl) | 1–10 | Strong Contrast |

EXAMPLE 4

Acoustic Characterisation (In vivo)

General procedure

Dry microparticle powders prepared as in Example 2 were redispersed in a sterile 0.9% (wt/wt) sodium chloride (aq) solution by shaking on a laboratory shaker for 12–16 hours.

The dispersions were injected in ear veins of chinchilla rabbits, and their contrast effect was measured using a Doppler technique in which an ultrasound probe was placed directly on a carotid artery and the inferior caval vein. Signal height in Doppler units and duration in seconds were recorded. The obtained signal heights were significant, indicating a strong in vivo ultrasound contrast effect for the dispersions. Long signal duration confirmed good in vivo stability.

| Example 4 | Particles from Example | Dry Matter [mg/ml] | Dose [mg/kg] | Artery | | Vein | |
|---|---|---|---|---|---|---|---|
| | | | | Peak (DU) | Duration (s) | Peak (DU) | Duration (s) |
| a | 2b | 10.6 | 1.8 | 2.6 | 14.7 | 2.7 | 159 |
| b | 2c | 9.9 | 1.7 | 7.5 | 156 | 8.0 | 324 |
| c | 2d | 9.9 | 1.7 | 6.0 | 96 | 5.5 | 252 |

What is claimed is:

1. A microparticulate powder useful as a contrast agent, said powder consisting of dry microparticles which consist of gas encapsulated by a non-polymeric and non-polymerisable solid or semi-solid substantially water-insoluble wall-forming material and a polymeric emulsifier.

2. A microparticulate powder as claimed in claim 1 wherein the wall-forming material is selected from fatty acids and esters thereof, fatty alcohols and esters thereof, fatty amines and amides thereof, lipophilic aldehydes and ketones, lipophilic derivatives of sugars, cholic acids and esters thereof, cholesterol and esters thereof, aliphatic and aromatic hydrocarbons, hydrophobically modified X-ray contrast agents and biocompatible fat-soluble antioxidants.

3. The microparticulate powder as claimed in claim 1 wherein the wall forming material contains one or more methylene diester units of Formula $$\{(O)_m\text{—CO—O—C}(R^1R^2)\text{—O—CO—}(O)_n\} \tag{I}$$

wherein $R^1$ and $R^2$ each represent a hydrogen atom or a carbon-attached monovalent organic group or $R^1$ and $R^2$ together form a carbon-attached divalent organic group and m and n are each selected from zero and 1.

4. The microparticulate powder as claimed in claim 3 wherein the wall-forming material contains one more methylene diester units of formula (I) in which $R^1$ and $R^2$ are selected from hydrogen atoms and methyl groups and n and m are both zero.

5. A microparticulate powder as claimed in claim 1 wherein the polymeric emulsifier is selected from polyvinyl alcohol, proteins, polysaccharides, block copolymers consisting of alternating hydrophilic and hydrophobic blocks, polyoxyethylated derivatives of partial fatty acid esters of hexahydric alcohols, polyvinylpyrrolidones, fatty alcohol ethers of polyoxyethylene alcohols, polyethylene glycol esters of fatty acids, polyethylene glycol-sorbitan-beeswax surfactants and perfluorinated derivatives of any of the above polyethylene glycol-containing compounds.

6. A microparticulate powder as claimed in claim 5 wherein the polymeric emulsifier is human serum albumin.

7. A method of generating enhanced images of a human or non-human animal body which comprises administering to said body a contrast agent comprising a dispersion of a microparticulate powder as claimed in claim 1 and generating an ultrasound or magnetic resonance image of at least a part of said body.

8. A process for the preparation of a microparticulate powder as claimed in claim 1 which comprises (i) generating a polymeric emulsifier-stabilized emulsion comprising hydrophilic and hydrophobic phases wherein wall-forming material is predominantly solubilised in the dispersed phase or about the interfaces between the phases and (ii) isolating dry microparticulate powder from said emulsion.

* * * * *